United States Patent [19]

See

[11] Patent Number: 5,091,192

[45] Date of Patent: Feb. 25, 1992

[54] BILE SALTS PERMANENTLY BOUND TO INSOLUBLE CELLULOSE AS A DIETARY SUPPLEMENT

[75] Inventor: Jackie R. See, Fullerton, Calif.

[73] Assignee: Natur-All Systems, Inc., La Mirada, Calif.

[21] Appl. No.: 465,917

[22] Filed: Jan. 16, 1990

[51] Int. Cl.$^5$ ............................................. A61K 35/413
[52] U.S. Cl. ................................... 424/528; 424/488; 424/494
[58] Field of Search ........................................ 424/528

[56] References Cited

U.S. PATENT DOCUMENTS

| | | | |
|---|---|---|---|
| 3,649,347 | 3/1972 | Battista | 177/144 |
| 4,407,795 | 10/1983 | Nicolau et al. | 424/180 |
| 4,447,412 | 5/1984 | Bilton | 424/16 |
| 4,533,542 | 8/1985 | Buddenbaum et al. | 424/31 |
| 4,590,170 | 5/1986 | Akiyoshi et al. | 436/533 |
| 4,597,762 | 7/1986 | Walter et al. | 623/1 |
| 4,602,005 | 7/1986 | Malinow | 514/26 |
| 4,747,881 | 5/1988 | Shaw et al. | 106/209 |
| 4,865,850 | 9/1989 | Shell et al. | 424/491 |

FOREIGN PATENT DOCUMENTS 2152379 4/1973 France.

Primary Examiner—Douglas W. Robinson
Assistant Examiner—Jean C. Witz
Attorney, Agent, or Firm—Christie, Parker & Hale

[57] ABSTRACT

In accordance with practice of the process of this invention, a composition is provided which is useful as a dietary supplement. The composition, which comprises bile salts permanently complexed with insoluble cellulose, upon ingestion by a human, facilitates passage of fats through the gastrointestinal tract and out from the body.

27 Claims, No Drawings 5,091,192

BILE SALTS PERMANENTLY BOUND TO INSOLUBLE CELLULOSE AS A DIETARY SUPPLEMENT

FIELD OF THE INVENTION

This invention relates to a composition for use as a dietary supplement which facilitates passage of fats through the gastrointestinal tract and out from the body, and to methods for producing and using the composition.

BACKGROUND OF THE INVENTION

Foods which are ingested by humans include various components, such as carbohydrates, proteins, fats, vitamins and minerals. To digest food, the stomach secretes gastric juice which is primarily an aqueous solution of hydrochloric acid and pepsin. The acid serves to chemically break down food particles, to activate pepsin (which digests protein), to stimulate pancreatic secretion (which includes, inter alia, the enzyme lipase to digest fats), and to aid mineral absorption. Because fat particles are not soluble in the aqueous solution of the stomach, they remain relatively large as they pass from the stomach into the small intestine, i.e., into the duodenum.

The action of the enzyme lipase is not efficient on fat particles of a size which exit the stomach. When a particle has a large size, its ratio of surface area to mass is small. Since the digestive action of lipase starts at the particle surface, fat is more readily digested if the fat particles are broken up into smaller particles or globules having a relatively higher surface area-to-mass ratio.

Bile, a product of the liver, contains bile salts which emulsify fat, i.e., the bile salts act as a detergent to split fat particles in the diet into smaller globules so that they remain suspended in water in the form of an emulsion. This exposes substantially more of the fat surface area to the lipase so that the digestion process is enhanced. The liver continuously produces bile, which is stored in the gallbladder prior to delivery into the small intestine.

When a meal contains fat, the gastrointestinal tract secretes cholecystokinin, which in turn stimulates the gallbladder to introduce bile into the small intestine. The bile salts contained in the bile break up the ingested fat into smaller globules, attach to the globules, and facilitate the passage of the small fat globules, called micelles, into the lymphatic system and, consequently, into the blood stream for alteration of the fat by the liver.

In the past, it has been suggested that bile (for example, animal bile from bovine or porcine sources) be attached to non-biodegradable particles, such as collagen or cellulose, to provide a dietary supplement. It was thought that the fat released from food in an animal's stomach would become attached to the bile on the non-biodegradable particles, which then would pass through the intestinal tract and out from the body through body excreta, such as body stool. Provision of such a composition would enable fat in the diet to pass into the stool and not into the bloodstream, thereby reducing the amount of calories available for use by the body, resulting in weight loss and reduction of serum lipids, i.e., cholesterols, triglycerides, and free fatty acids.

In order for the non-biodegradable/bile composition to function effectively to carry fat particles through the gastrointestinal tract and out from the body, the bile salts must be permanently complexed or affixed to the non-biodegradable particles. If the bile salt is not permanently attached, the bile salt and associated fat micelles, instead of passing through the intestinal tract and out from the body, will be absorbed into the bloodstream through the intestinal mucosa.

It has been found that, with prior diet supplements that purport to incorporate bile bound to a non-biodegradable matrix, less bile is permanently affixed than desired. This results in inefficient removal of fat from the body.

There is a need, therefore, for a composition for use as a dietary supplement which is produced by a method which results in maximizing the amount of bile salts that are permanently affixed to a non-biodegradable substance.

SUMMARY OF THE INVENTION

The present invention relates to compositions for use as dietary supplements and to methods to producing such supplements, wherein the compositions comprise bile salts permanently bound to insoluble cellulose. In an exemplary embodiment, the composition-forming method comprises two stages; a first stage in which an activated composition comprising bile salts and insoluble cellulose is formed, and a second stage in which the bile salts are permanently bound or complexed with the insoluble cellulose.

The activated composition of the first stage is formed by mixing together bile salt and insoluble cellulose in the dry state to form a bile salt/insoluble cellulose mixture. The bile salt/insoluble cellulose mixture is blended into distilled water adjusted to a pH of from about 2 to about 4 to form a bile salt/insoluble cellulose suspension. Preferably, the pH of the suspension is about 3. The bile salt/ insoluble cellulose suspension is then dried at a sufficient temperature and for a sufficient time, while being stirred, to provide a partially dry, activated bile salt/insoluble cellulose composition having a selected moisture content. Preferably, the moisture content of the dried composition is no less than about 1% by weight up to about 3% by weight, based on the total dry weight of the composition. The partially dry, activated composition is granulated to provide an activated bile salt/insoluble cellulose composition of a selected particle size.

In the second stage, the partially dry, activated, granulated bile salt/insoluble cellulose composition is mixed or blended with microcrystalline cellulose to provide the composition of the invention which comprises bile salt that is permanently affixed to or complexed with the insoluble cellulose.

In a preferred embodiment of practice of the present invention, ox bile extract is used in the first stage, and methyl cellulose is added along with insoluble cellulose. In the second stage, it is preferred that various plant fibers and methyl cellulose are added along with microcrystalline cellulose.

The dietary supplement composition provided in accordance with this invention, comprising bile salts permanently bound or complexed with insoluble cellulose, is administered to a human for sequestering fats released from food in the gastrointestinal tract and for promoting removal of the fats from the body. After the composition is administered and enters the gastrointestinal tract, the fats released from food in the gastrointestinal tract are allowed to become attached to the insoluble cellulose/bile salt complex. The fat-laden insoluble cellulose/bile salt complex is thereafter permitted to pass through the gastrointestinal tract and out of the body with body excreta.

DETAILED DESCRIPTION

The dietary supplement provided in accordance with practice of principles of the present invention comprises a composition which includes bile salts irreversibly bound or complexed with insoluble cellulose. If desired, the composition can also include plant fiber.

As used herein, the term "insoluble cellulose" means cellulose which can pass through the gastrointestinal system of a human without being biodegraded, i.e., without being altered chemically or solubilized. Additionally, the insoluble cellulose useful in accordance with practice of this invention has a particle size which is sufficiently large so that the particles will not pass through the surface mucosa of the gastrointestinal tract. It is preferred that the insoluble cellulose particles are at least about 2 microns in size and, more preferably, the particles are at least 5 microns in size. Usually, the particles will be of a size of less than about 100 microns. When particles greater than about 100 microns are used, there is less than the desired amount of surface area for complexing the bile salts. Such insoluble cellulose includes powdered cellulose, provided by James River Corporation of Borlin, N.H., under the trademark "SOLKA FLOC BW-300FCC".

As used herein, the term "soluble cellulose" means cellulose that is soluble in water. Such soluble cellulose includes methyl cellulose which, although insoluble in water at high temperatures, is soluble at temperatures below about 120° F.

As used herein, the term "microcrystalline cellulose" refers to a non-fibrous form of cellulose in which the cell wall of the fibers have been broken into fragments ranging in size from a few hundred microns to a few tenths of a micron in length. Such microcrystalline cellulose includes a product provided by FMC Corporation of Philadelphia, Pa., identified by the trademark "AVICEL pH102".

As used herein, "plant fiber" or "fiber" includes pectins, oat fiber, beet fiber, apple fiber, orange fiber, grapefruit fiber, carrot fiber, rice fiber, and the like.

The dietary supplement composition of the present invention may be orally administered, for example, with inert adjuvants or with an edible carrier, or may be enclosed in hard- or soft-shelled gelatin capsules, or may be compressed into tablets, or may be incorporated directly with food. In one exemplary embodiment of practice of the present invention, the composition is compressed into tablets in the presence of a mixture of biologically inert adjuvants comprising lubricants, fillers and coatings. Acceptable lubricants can comprise mixtures of hydrogenated vegetable oils of conventional pharmaceutical grade and fatty acids salts, for example, magnesium stearate, stearic acid, palmitic acid, and the like. Fillers can include silicon dioxide, di-calcium phosphate dihydrate, methyl cellulose or cross linked methyl cellulose.

A key feature of the present invention is the discovery of a process which results in increased amounts of bile salts being irreversibly or permanently bound to an insoluble cellulose component of the composition compared to prior-art processes and the compositions produced thereby.

In an exemplary embodiment of the present invention, the process for producing the dietary supplement is conducted in two stages or steps. In the first stage of the process, a matrix of bile salt and insoluble cellulose is prepared by mixing together desiccated bile and insoluble cellulose in the dry state and then blending the mixture into distilled water in a blender to provide a bile/insoluble cellulose suspension. In a preferred embodiment, ox bile is used, but bile from other sources, such as porcine bile, other bovine bile, other animal bile, sodium choleate and sodium cholate, can be used, if desired. Ox bile useful in accordance with this invention is provided under the following trademarks: "BICOL", "BILEIN", "BILICHOLAN", "CHOLATOL", "COLALIN", "CRESCEFEL", "DESICOL", "DOXYCHOL", "GLYCOTAURO", "PANOXOLIN", "PLEBILIN", AND "VALACHOL".

After the bile salt/insoluble cellulose matrix is mixed together in the aqueous suspension, the matrix is dried while stirring in a heated stirring device to provide a partially dry matrix of ox bile and insoluble cellulose, having a selected amount of moisture remaining. In a preferred embodiment, the moisture remaining is from about 1% by weight to about 3% by weight compared to the total dry weight of the matrix. The partially dry ox bile/insoluble cellulose matrix is then mixed with microcrystalline cellulose which results in a permanent binding or complexing of bile salts contained in the ox bile to the insoluble cellulose. Mixing the ox bile/insoluble cellulose matrix with the microcrystalline cellulose is called "wet" compounding or mixing herein because the matrix contains greater than 1 wt % moisture.

As is described below in greater detail, it has been found that, if ox bile, insoluble cellulose, and microcrystalline cellulose are mixed together in a single step, there is less than the desired amount of permanent binding between the bile salts and the insoluble cellulose. Not being bound by the theory, it is thought that the bile salt/insoluble cellulose matrix or composition resulting from the first stage of the process of the invention is "activated" to thereby facilitate the permanent binding or complexing of bile salts to the cellulose in the second stage. Thus, the bile salt/insoluble cellulose composition resulting from the first step or stage of the process of the present invention is called the "activated" bile salt/insoluble cellulose composition or "activated composition".

It has been found that the conditions under which the process of the present invention is carried out are critical to facilitate the desired amount of permanent binding of the bile salts to the insoluble cellulose.

In an exemplary embodiment of a first stage of the process for producing the dietary supplement of the present invention, desiccated ox bile comprising bile salts is mixed together dry with insoluble cellulose and soluble cellulose. Distilled water, adjusted to a pH of from about 2 to about 4 with hydrochloric acid, is then added to a blender along with the bile salt/insoluble cellulose/ soluble cellulose mixture to provide an ox bile/insoluble cellulose suspension. Preferably, the pH is about 3. The suspension is heated to about 45° C. and blended for about 30 minutes. Preferably, at least about ½ gram of ox bile are used per gram of insoluble cellulose in the first stage. It is also preferred that the weight of insoluble cellulose to the weight of soluble cellulose is in a ratio of about 4 to 1.

The ox bile/insoluble cellulose suspension is then poured from the blender into a heated stirring machine and is mixed or stirred at a temperature of at least about 45° C. for from about 1 to about 12 hours to provide an activated bile salt/insoluble cellulose composition. During the stirring process, drying takes place. The activated composition, while being stirred, is dried to a moisture content of less than about 3% by weight of water but not less than about 1%. If the water content of the bile salt/insoluble cellulose composition is reduced to less than about 1%, its "activation" is relatively less, and permanent complexing of the bile salts to the insoluble cellulose is less than desired in the second stage. If more than about 3% water remains, compression into a tablet after the second stage is inhibited. Preferably, the activated composition is dried to about 2 wt % moisture. When the temperature used during drying is higher, shorter drying and stirring times are required, while lower temperatures require longer drying times. For example, when the temperature is 45° C., the composition is stirred for at least about 12 hours. Conversely, for example, when the temperature is 170° C., the composition is stirred for 1 hour. If the temperature is less than about 45° C., little or no activation occurs and, hence, there is little or no permanent complexing in the second stage. If the temperature is greater than about 170° C., it is approaching the melting point of bile salts and a portion will be lost as vapor, thereby decreasing the efficiency of the process.

After the activated composition has been dried to contain from less than 3 wt % to more than 1 wt % water, it is called the "partially dry, activated bile salt/insoluble cellulose composition", or the "partially dry, activated composition". The partially dry, activated composition is granulated to provide an activated bile salt/insoluble cellulose composition of a selected particle size. Preferably, the particle size is 12 mesh or less. (Based on the Tyler Standard sieve series; the sieve opening of a 12-mesh screen is 1.41 mm.) If the particle size is greater than about 12 mesh, the surface area to volume ratio is not sufficiently large to provide the desired amount of surface area for activation.

The activated, granulated composition from the first stage is mixed in a second stage with microcrystalline cellulose in a blender, such as a blender provided by the Hamilton Beach Company under the trade name "DRINKMASTER", or a Waring blender, or the like. The amount of microcrystalline cellulose added to the second stage is at least about 0.4 gram per gram of ox bile used in the first stage. If desired, other materials, such as methyl cellulose and/or plant fiber, or chitin or chitosan, can be blended with the microcrystalline cellulose and the partially dry, activated, granulated composition from the first stage. Preferably, the amount of methyl cellulose added is about 0.1 to 0.2 gram per gram of ox bile used in the first stage. The amount of fiber added can be from about 0.1 gram to about 3 grams per gram of ox bile used in the first stage.

If it is desired that the dietary supplement provided in accordance with this invention be administered in the form of a tablet, a mixture of biologically inert adjuvants comprising lubricants and fillers is mixed in the second stage with the partially dry, activated bile salt/insoluble cellulose composition, the microcrystalline cellulose, and the methyl cellulose and plant fiber (if used). The composition is then formed into tablets using standard tablet-forming techniques.

Tablets provided in accordance with this invention preferably comprise from about 20%–35% by weight ox bile, 45%–60% by weight insoluble cellulose, 5%–15% by weight 0 soluble cellulose, and 5%–25% by weight microcrystalline cellulose, with the percentages based on the total weight of ox bile, insoluble cellulose, soluble cellulose and microcrystalline cellulose. More preferably, the tablets provided in accordance with this invention comprise about 26 wt % ox bile, 52 wt % insoluble cellulose, 12 wt % soluble cellulose, and 10 wt % microcrystalline cellulose, based on the total weight of ox bile, soluble cellulose, insoluble cellulose and microcrystalline cellulose. Tablets provided in accordance with this invention which incorporate plant fiber, and taking the excipients into account, preferably include about 10% by weight plant fiber and 10% by weight excipients, based on the total weight of the tablet.

In an example of administration of the dietary supplement provided in accordance with practice of the present invention, two tablets of a weight of about 780 mgs are taken 30 minutes before a meal to facilitate dissolution prior to presentation of the fat in the diet to the gastrointestinal system. This procedure is repeated prior to each meal for a four-week period. During the time that the dietary supplement is used, fats released from food in the gastrointestinal tract become attached to the insoluble cellulose/bile salt complex. The fat-lade insoluble cellulose/bile salt complex then passes through the gastrointestinal tract and out from the body with body excreta.

The invention is further illustrated but is not intended to be limited by the following examples.

Examples 1 through 6 describe methods used in attempts to permanently attach ox bile to cellulose in a one-stage process.

EXAMPLE 1

A dietary supplement tablet was prepared by mixing together 165 milligrams (mgs) of desiccated ox bile extract (provided by American Laboratories, Inc., of Omaha, Nebraska, as Lot No. 348773), 100 mgs of acacia powder, 165 mgs of powdered cellulose ("SOLKA FLOC BW-300FCC"), 100 mgs of beet fiber (provided by D. D. Williamson & Co., Inc., of Piscataway, N.J., under the trademark "FIBREX"), 65 mgs of apple fiber (provided by Triarco, Inc., of Paterson, N.J., under Lot No. 13693), 80 mgs of microcrystalline cellulose ("AVICEL pH102"), and 175 mgs of excipients, including 25 mgs of magnesium stearate (provided by VGF Chemical Company, of New York, N.Y., as "Magnesium Stearate-NF"), 130 mgs of methyl cellulose (provided by Dow Chemical Co. of Midland, Mich., under the trademark "METHOCEL K-15M") and 20 mgs of silicon dioxide (provided by the Degussa Corporation of West Germany, under the trademark "SIPERNAT 22-S"). The mixture was blended together dry and pressed into a tablet of a weight of 850 mgs. The tablet was heated with a dry heat to 45° C. for 1 hour.

EXAMPLE 2

The procedure of Example 1 was repeated, except that microcrystalline cellulose was eliminated from the formulation.

EXAMPLE 3

A dietary supplement tablet was prepared by mixing together 165 mgs of desiccated ox bile extract (Lot No. 348773 from American Laboratories, Inc.), 265 mgs of powdered cellulose ("SOLKA FLOC BW-300FCC"), 80 mgs of methyl cellulose ("METHOCEL K-15M"), 50 mgs of beet fiber ("FIBREX"), 50 mgs of oat fiber (provided by D. D. Williamson & Co., Inc., of Louisville, Ky., under the trademark "BETTER BASICS Standard Oat Fiber 757"), 50 mgs of apple fiber (Lot No. 13693 from Triarco, Inc.) and 90 mgs of excipients, including 25 mgs of di-calcium phosphate dihydrate (provided by Chemesche Fabrigue of Budenheim, West Germany, under the trademark "DI-CAFOS"), 20 mgs of magnesium stearate ("Magnesium Stearate NF"), 20 mgs of silicon dioxide ("SIPERNAT 22S") and 25 mgs of methyl cellulose ("METHOCEL K-15M"). The ingredients were mixed at room temperature for 5 minutes into 165 milliliters (mls) of distilled water and 10 mls of 6 normal hydrochloric acid to provide a suspension having a pH of 3. The mixture was dried at 45° C. for 4 hours and, after drying, the material was compressed into a tablet.

EXAMPLE 4

A dietary supplement tablet was prepared by mixing together 165 mgs of crushed desiccated ox bile extract (Lot No. 348773 from American Laboratories, Inc.), 100 mgs acacia powder, 169 mgs barley/rice fiber mixture, 20 mgs citrus pectin fiber (provided by Freeman Industries, Inc., of Tuchahoe, N.Y., called "Citrus Pectin Cellulose Complex"), 15 mgs carrot fiber, 5 mgs acerola powder (provided by Pharmachem Laboratories, Inc., of So. Hackensack, N.J., called "Powdered Extract Acerola 1:4"), 20 mgs of methyl cellulose ("METHOCEL K-15M"), 165 mgs of powdered cellulose ("SOLKA FLOC BW-300FCC"), and 40.2 mgs of excipients, including 15 mgs of silicon dioxide ("SIPERNAT 22S"), 18.2 mgs of stearic acid (provided by Generichem Corporation called "Stearic Acid-NF, Lot 266"), and 7 mgs of magnesium stearate (provided by VGF Chemical Corporation of New York, N.Y., as "Magnesium Stearate NF").

All of the ingredients, except the excipients, were mixed for 5 minutes in the dry state. Then 165 mls of distilled water were added, and the pH was adjusted to 4 using a 6 normal hydrochloric acid solution. The hydrated mixture was then heated at 45° C. for one hour with constant stirring. Just before heating and mixing, the excipients were added. The material was dried at room temperature for one hour and then compressed into tablet form. The tablets were coated with equal amounts of chromaseal (3 mgs), methyl cellulose (3 mgs) ("METHOCEL K-15M"), and carnauba wax (3 mgs).

EXAMPLE 5

A dietary supplement was prepared by mixing together 41.25 grams of desiccated ox bile extract (Lot No. 348773 from American Laboratories, Inc.), 76.25 grams of microcrystalline cellulose ("AVICEL-pH102") for a total dry weight of 117.5 grams. The mixture was stirred for 4 to 5 minutes, at which time 500 grams of distilled water, plus 7.5 grams of 6 normal hydrochloric acid at a water bath temperature of 25° C., was added. The resulting solution had a pH of 2.85. After stirring for 1½ hours at 70° C., the solution showed a pH of 3.07. The solution was heated with constant stirring in a water bath at 70° C for 4 hours and then cooled to room temperature. The mixture was filtered, and the filtrate was washed with potassium biphthalite 0.05 M. The supernatant was diluted to 1000 mls.

EXAMPLE 6

A dietary supplement tablet was prepared by mixing together 165 mgs of desiccated ox bile extract (Lot No. 348773 from American Laboratories, Inc.), 100 mgs of acacia powder, 165 mgs of powdered cellulose ("SOLKA FLOC BW-300FCC"), 100 mgs of beet fiber ("FIBREX"), 65 mgs of apple fiber (Lot No. 13693 from Triarco, Inc.), 80 mgs of microcrystalline cellulose ("AVICEL"), and 175 mgs of excipients, including 122.5 mgs methyl cellulose ("METHOCEL K-15M"), 22.5 mgs of di-calcium phosphate dihydrate ("DICAFOS"), 15 mgs of magnesium stearate ("Magnesium Stearate NF"), and 15 mgs of silicon dioxide ("SIPERNAT 22S"). The mixture was stirred in dry form for 30 minutes, and then 165 mls of distilled water were added and the pH adjusted to 3 using a 6 normal hydrochloric acid. The mixture was heated at 45° C. for 1 hour, which dried it completely. After drying, the material was compressed into a tablet.

Example 7 discloses preparation of a dietary supplement tablet in accordance with an exemplary embodiment of the two-stage process of the present invention by blending ox bile, insoluble cellulose and soluble cellulose in a water medium at a pH of 3.9 in the first stage to form an ox bile/cellulose matrix. The ox bile/cellulose matrix was partially dried and granulated. The granulated material from the first stage was wet compounded., i.e., the material from the first stage with at least 1 wt % water content was blended with microcrystalline cellulose, plant fibers, methyl cellulose and excipients. The compounded material was formed into a tablet.

EXAMPLE 7

165 mgs of crushed desiccated ox bile extract (Lot. No. 348773 from American Laboratories, Inc.) was mixed with 70 mgs of methyl cellulose ("METHOCEL K-15M") and 265 mgs of powdered cellulose ("SOLKA FLOC BW-300FCC") and blended together in the dry state for 5 minutes. After the medium was mixed, 167 mls of deionized water were added, along with 10 mgs of concentrated HCL, to adjust the pH to 3.9 to form a suspension of ox bile extract, methyl cellulose and powdered cellulose. The suspension was stirred for 30 minutes at 45° C. by means of a blender ("DRINKMASTER").

The suspension was then dried, while being stirred in a heated stirring machine, at 45° C. for 12 hours, during which time the moisture content of the mass was monitored. Drying was discontinued when the moisture content was 2% by weight compared to the total weight of the ingredients. The partially dry material, i.e., material with about 2% moisture was reground by means of a mortar and pestle to provide a granulated mass having a particle size of less than 12 mesh, i.e., less than a size of 1.14 mm. The granulated mass was then placed into a blender and 50 mgs of oat fiber ("BETTER BASICS"), 10 mgs of methyl cellulose ("METHOCEL K-15M"), 50 mgs of beet fiber ("FIBREX"), 50 mgs of apple pectin (Lot. No. 13693 from Triarco, Inc.), 70 mgs of microcrystalline cellulose ("AVICEL-pH102"), 20 mgs of di-calcium phosphate dihydrate ("DI-CAFOS"), 20 mgs of magnesium stearate ("Magnesium Stearate NF") and 10 mgs of silicone dioxide ("SIPERNAT 22S") were added to the blender. The mixture was blended for 15 minutes at room temperature and then recovered.

The mixture was compressed into a tablet which weighed 780 mgs using approximately 24,000 pounds per square inch of pressure. The tablet was then coated with #5 pharmaceutical glaze NF by using standard coating techniques.

In Examples 8 through 12 below, the amount of bile salt that is permanently complexed or bound with the insoluble cellulose components of the tablets prepared in Example 1, 2, 4, 6, and 7 is shown.

EXAMPLE 8

Amount of Bile Salt Permanently Bound in the Tablets of Example 1

A compressed tablet provided in accordance with the process of Example 1 was crushed in a dry state with a mortar and pestle and placed in 50 mls of water which had been adjusted to a pH of 3 using 6 normal hydrochloric acid. The sample was vigorously vortexed (shaken) for complete suspension and allowed to sit for 30 minutes. The supernatant was then separated from the solid components by means of decantation. The amount of bile salt in micromoles (measured in terms of cholic acid) found in the supernatant per liter of solution was determined using an autoanalyzer provided by Beckman Instruments Company of Fullerton, California, and sold under the trademark "SYNCHRON CX5".

The procedure was repeated twice by crushing second and third tablets provided in accordance with the process of Example 1 separately into a 50-ml container of water adjusted to pH's of 7 and 11, respectively, using sodium hydroxide. The tests were conducted at pH's of 3, 7, and 11 to simulate conditions in the gastrointestinal tract. For example, the stomach pH is 1.5 to 3, and the pH of the small intestine is usually alkaline, usually from about 11 to 12. Thus, in the gastrointestinal tract, the composition will be subjected to pH's in the range of 3 to 11.

The amount of micromoles of bile salt per liter of solution for the experiments done at pH's of 3, 7, and 11 are as follows:

| pH | Micromoles of Bile Salt Per Liter of Supernatant |
|---|---|
| 3 | 219.3 |
| 7 | 227.8 |
| 11 | 225.0 |

These numbers were compared to a control experiment which was run to determine the amount of bile salt present in an aqueous solution of ox bile in the absence of any other components.

The control was run by placing 165 mgs of ox bile extract (Lot No. 348773 from American Laboratories, Inc.) in 50 mls of distilled water adjusted to a pH of 3 using 6 normal hydrochloric acid. The sample was vortexed for complete suspension and then allowed to sit for 30 minutes. The supernatant was drawn off at room temperature for analysis on the autoanalyzer ("SYNCHRON CX5"). It was determined that there were 272 micromoles of ox bile per liter. A duplicate experiment was run, and it was found that there were 290.8 micromoles of ox bile per liter.

The same procedure was repeated twice (in duplicate), except that the pH's of the water into which the ox bile was dissolved was adjusted to 7 in one experiment and adjusted to 11 in the other. The amount of bile salt per liter in the supernatant for the experiments of pH 3, 7, and 11 is as follows:

| pH | Average Micromoles of Bile Salt Per Liter (Runs 1 and 2) |
|---|---|
| 3 | 281.4 |
| 7 | 313.3 |
| 11 | 309.1 |

The calculation of the amount of bile salt that is permanently bound to insoluble cellulose in the tablets provided by the process of Example 1 was done by subtracting the micromole/liter figure of the experimental run at the given pH from the micromole/liter figure of the control at the same pH. The calculated number was converted to the percent of bile salt bound by dividing it by the number of micromoles/liter figure of the control.

The percent of permanently bound bile salt for the 3, 7, and 11 pH runs of Example 8 is as follows:

| pH | Percent of Bile Salt Bound to Matrix |
|---|---|
| 3 | 30.0% |
| 7 | 28.0% |
| 11 | 28.0% |

EXAMPLE 9

Amount of Bile Salt Permanently Bound In the Tablets of Example 2

The procedure of Example 8 was repeated, except that tablets provided in accordance with the process of Example were used. The amount of micromoles of bile salt per liter of solution for the experiments done at pH's of 3, 7, and 11 are as follows:

| pH | Micromoles of Bile Salt Per Liter as Supernatant |
|---|---|
| 3 | 189.3 |
| 7 | 188.0 |
| 11 | 179.8 |

The percent of permanently bound bile salt for the 3, 7, and 11 pH runs of Example 9 was calculated to be as follows:

| pH | Percent of Bile Salt Bound to Matrix |
|---|---|
| 3 | 32.7% |
| 7 | 39.9% |
| 11 | 41.2% |

EXAMPLE 10

Amount of Bile Salt Permanently Bound in the Tablets of Example 4

The procedure of Example 8 was repeated, except that tablets provided in accordance with the process of Example were used. The amount of micromoles of bile salt per liter of solution for the experiments done at pH's of 3, 7, and 11, run in triplicate, are as follows:

| | Micromoles of Bile Salt Per Liter as Supernatant | | | |
|---|---|---|---|---|
| pH | Run 1 | Run 2 | Run 3 | Average (Runs 1,2,3) |
| 3 | 215.0 | 209.8 | 185.1 | 203.3 |
| 7 | 237.4 | 250.0 | 246.5 | 244.6 |
| 11 | 163.3 | 246.5 | 241.4 | 217.1 |

The percent of permanently bound bile salt for the 3, 7, and 11 pH runs (on average) of Example 10 was calculated to be as follows:

| pH | Percent of Bile Salt Bound to Matrix |
|---|---|
| 3 | 28% |
| 7 | 22% |
| 11 | 30% |

EXAMPLE 11

Amount of Bile Salt Permanently Bound In the Tablets of Example 6

The procedure of Example 8 was repeated, except that compressed tablets provided in accordance with the process of Example 6 were used. The amount of micromoles of bile salt per liter of solution for the experiments done at pH's of 3, 7, and 11 are as follows:

| pH | Micromoles of Bile Salt Per Liter as Supernatant |
|---|---|
| 3 | 219.3 |
| 7 | 227.8 |
| 11 | 225.0 |

The percent of permanently bound bile salt for the 3, 7, and 11 pH runs of Example 9 was calculated to be as follows:

| pH | Percent of Bile Salt Bound to Matrix |
|---|---|
| 3 | 23% |
| 7 | 28% |
| 11 | 28% |

EXAMPLE 12

Amount of Bile Salt Permanently Bound in the Tablets of Example 7

The procedure of Example 8 was repeated, except that compressed tables provided in accordance with the process of Example 7 were used. The amount of micromoles of bile salt per liter of solution for the experiments done at pH's of 3, 7, and 11 are as follows:

| pH | Micromoles of Bile Salt Per Liter as Supernatant |
|---|---|
| 3 | 115.6 |
| 7 | 157.4 |
| 11 | 138.2 |

The percent of bound bile salt was calculated to be as follows:

| pH | Percent of Bile Salt Bound to Matrix |
|---|---|
| 3 | 59.0% |
| 7 | 50.0% |
| 11 | 56.0% |

Examples 8 through 12 clearly show that the greatest amount of permanent binding of bile salt to the insoluble cellulose was achieved by the two-stage process of the present invention.

Examples 13 and 14 are directed to clinical trials showing the results of the use of a dietary supplement formulated using a one-step process and a supplement provided in accordance with practice of the present invention.

EXAMPLE 13

The subject of the clinical trial of this example was a 63-year-old female with a prior history of combined hyperlipidemia and coronary artery bypass surgery and coronary angioplasty for unstable angina pectoris. On entry into the trial, the subject's weight was 222½ pounds, and her measurements were: waist, 39 inches; hips, 47½ inches; right arm, 15 inches; left arm, 14½ inches; right thigh, 25 inches; and left thigh, 25½ inches. The subject was counselled regarding the protocol and was asked to be on an ad lib diet. She began the trial 10 days later after counselling and a wash-in period, during which time binge eating and drinking alcohol were reduced.

After the 10-day wash-in period, the subject weighed 217 pounds, and her measurements were: waist, 37½ inches; hips, 45¾ inches; right arm, 14¾ inches; left arm, 13¾ right thigh, 24¼ inches; and left thigh, 25 inches. At this time, lipid studies in a fasting state showed a total cholesterol 209 mgs/dl, LDL 123 mgs/dl, HDL 50 mgs/dl and triglycerides 179 mgs/dl. The cholesterol upper limits of normal in this laboratory are 200 mgs/dl, and triglycerides are 170 mgs/dl, LDL 170 mgs/dl, HDL 85 mgs/dl. The subject took two tablets provided by the "one-step" process of Example 4 one-half hour before mealtime, even if no meal was consumed, with a full 8-ounce glass of water. The subject's weight at the end of each week of the trial was as follows: week one, 215 pounds; week two, 212½ pounds; week three, 210 pounds; week four, 209½ pounds; week five, 209 pounds; and week six, 209 pounds. At the end of week six, the measurements of the subject were: waist, 36 inches; hips, 45 inches; right arm, 14 inches; left arm, 13 inches; right thigh, 24 inches; and left thigh, 24⅛ inches. The lipid serum studies were repeated in a fasting state, and at the end of week 6 were as follows: total cholesterol, 205, a reduction of 4 mgs/dl; LDL, 137, an increase of 14 mgs/dl; HDL, 37, a reduction of 13 mgs/dl; triglycerides, 156, a reduction of 23 mgs/dl. At the end of week six, there had been an 8-pound weight loss on an ad lib diet. Total serum cholesterol was still abnormal and only reduced by less than 2%. Disturbingly, LDL cholesterol (the harmful form) was increased by 14 mgs/dl or an increase of about 10%. Additionally disturbing was the reduction of HDL by 13 mgs/dl, a 26% reduction from 50 to 37. The triglycerides reduced 13%, but were still abnormal.

At this point, it was determined that the tablets provided by the process of Example 4 did not have a desirably high percentage of complexing of bile salt to cellulose/fiber. In fact, absorption of bile salts in the body from the Example 4 formulation is indicated by an increase in the LDL, decrease in the HDL, and small decrease in cholesterol and triglycerides despite an 8-pound weight loss. At the end of week 6, the trial using the tablets of Example 4 was terminated.

The subject was then switched to tablets provided in accordance with the procedure of Example 7, (the tablets provided in accordance with practice of this invention). At the time the subject started taking the tablets formulated in accordance with Example 7, she weighed 209 pounds, and had the same measurements and serum lipids as at the time of termination of the earlier study. The subject took two tablets three times a day with an 8-ounce glass of water 30 minutes before meals, with or without eating The subject's weight at the end of each week of the trial was as follows: week one, 207 pounds; week two, 205¾ pounds; week three, 205¾ pounds;, week four, 205 pounds; with a 4-pound weight loss overall. The subject's measurements at the end of the second portion of the study compared to the measurements at the termination of the first portion were as follows: waist reduced from 36 inches to 34¾ inches, hips reduced from 45 inches to 44¾ inches, right arm reduced from 14 inches to 13 inches, left arm reduced from 13 inches to 12½ inches, right thigh reduced from 24 to 23 inches, and left thigh reduced from 24½ to 24 inches.

Most significantly, after 4 weeks on tablets made according to the process of the invention, total cholesterol was reduced from 205 to 185 mgs/dl, despite a weight loss of 4 pounds. This is a fairly dramatic reduction of over 10%. Encouragingly, LDL went from 137 mgs/dl to 92 mgs/dl, a reduction of 45 mgs/dl or approximately a 32% reduction. In addition, HDL cholesterol rose from 37 to 40 mgs/dl, an increase of approximately 9%, and the triglycerides rose to 263 mgs/dl from 156 mgs/dl or a rise of 107 mgs/dl, (60%) while remaining abnormal. These serum lipids definitely reveal a significant beneficial cholesterol effect, indicating that the bile salts cellulose/fiber is truly inhibiting cholesterol absorption in the gut.

EXAMPLE 14

The subject of the clinical trial of this example was a 45-year-old male with a prior history of combined hyperlipoproteinemia, coronary artery bypass surgery times two, and angina pectoris. On entry into the trial, the subject weighed 310 pounds, and his measurements were: waist, 55½ inches; hips, 57 inches; right arm, 16½ inches; left arm, 15½ inches; right thigh, 26 inches; and left thigh, 25½ inches The subject was counselled regarding the protocol and was asked to be on an ad lib diet. After a 10-day wash-in and education period, the subject weighed 302 pounds, and his measurements were: waist, 55 inches; hips, 56½ inches; right arm, 16½ inches; left arm, 15½ inches; right thigh, 26 inches; and left thigh 25½ inches. At this time, lipid studies in a fasting state showed total cholesterol 377 mgs/dl, LDL 297 mgs/dl, HDL 51 mgs/dl, and triglycerides 147 mgs/dl.

The subject followed the same procedure as the subject of Example 13, taking two tablets, provided in accordance with the process of Example 4, one-half hour before meals three times a day, even if he did not have a meal, with a full 8-ounce glass of water. The subject's weight at the end of each week of the trial was as follows: week one, 00 pounds; week two, 295 pounds; week three, 305 pounds; week four, 305 pounds; week five, 302 pounds; and week six, 13 pounds, for a weight gain of 11 pounds overall. At the end of week six, the subject's measurements were: waist, 54½ inches; hips, 56½ inches; arms, 16½ inches; right thigh, 26 inches; and left thigh, 25½ inches.

The lipid studies repeated in the fasting state at the end of week 6 showed the following: total cholesterol was 439, an increase of 62 mgs/dl (disturbingly, an increase of 21% of this harmful LDL fraction); the HDL was reduced from 51 to 29, a reduction of 22 mgs/dl, a significant reduction of 43%; and triglycerides were 249, up from 147, an increase of 102 mgs/dl, for a 69% increase.

The subject was then switched to tablets provided in accordance with the procedure of Example 7, (the tablets provided in accordance with practice of this invention). At the time the subject started taking the Example 7 tablets, he weighed 313 pounds, and his measurements were: waist, 54¼ inches; hips, 56½ inches; right arm, 16¼ inches; left arm, 15½ inches; right thigh, 26 inches; subject's serum lipids were as follows: total cholesterol, 439 mgs/dl; LDL, 360 mgs/dl; HDL, 29 mgs/dl; and triglycerides 249 mgs/dl. The subject took two tablets three times a day with an 8-ounce glass of water, with or without eating. The subject's weight at the end of each week of the trial was as follows: week two, 309 pounds; week three, 295 pounds; week four, 290 pounds; and week five, 285 pounds, for a reduction of 28 pounds. The subject's measurements were: waist, 52 inches; hips, 54½ inches; right arm, 15½ inches; left arm, 15½ inches; right thigh, 24 inches; and left thigh, 23½ inches. At the end of week four of the second portion of the study, the subject's fasting serum lipids were: total cholesterol, 341 mgs/dl; LDL, 156 mgs/dl; HDL, 29 mgs/dl; and triglycerides, 122 mgs/dl.

By taking the tablets provided in accordance with the present invention, the subject's measurements showed a reduction and his total serum cholesterol was reduced 22%, the LDL fraction 57%, the HDL unchanged, with a 51% reduction in triglycerides. The changes were all significant and of benefit to the subject.

The above description of exemplary embodiments of the methods used for preparing compositions for use as dietary supplements and the dietary supplements produced thereby are for illustrative purposes. Because of variations which will be apparent to those skilled in the art, the present invention is not intended to be limited to the particular embodiments described above. The scope of the invention is defined in the following claims.

What is claimed is:

1. A method for producing a dietary supplement comprising bile salts permanently bound to insoluble cellulose, the method comprising the steps of:

(a) in a first stage, forming an activated composition of bile salts and insoluble cellulose by:

(i) mixing together bile salt and insoluble cellulose in the dry state to form a bile salt/insoluble cellulose mixture;

(ii) blending the bile salt/insoluble cellulose mixture into distilled water adjusted to a pH of from about 2 to about 4 to form a bile salt/insoluble cellulose suspension;

(iii) drying the bile salt/insoluble cellulose suspension to no less than 1% moisture by weight of composition, while stirring, to provide a partially dry, activated bile salt/insoluble cellulose composition; and (iv) granulating the partially dry, activated composition to provide an activated bile salt/insoluble cellulose composition; and (b) in a second stage, mixing the partially dry, activated, granulated bile salt/insoluble cellulose composition from the first stage with microcrystalline cellulose to provide a composition from the first stage with microcrystalline cellulose to provide a composition comprising bile salts permanently affixed to the insoluble cellulose composition.

2. The method according to claim 1 wherein the bile salt/insoluble cellulose suspension is dried at a temperature of at least 45° C. for from about 1 to about 12 hours.

3. The method according to claim 1 wherein the bile salt/insoluble cellulose suspension is dried at 45° C. for about 12 hours.

4. The method according to claim 1 herein the pH of the bile salt/insoluble cellulose suspension is about 3.

5. The method according to claim 1 wherein the partially dry, activated bile salt/insoluble cellulose composition has a moisture content of from about 1% by weight to about 3% by weight compared to the total dry weight of the composition.

6. The method according to claim 1 wherein methyl cellulose is mixed together in the dry state with the insoluble cellulose and desiccated bile.

7. The method according to claim 1 wherein the bile salt is provided by ox bile.

8. The method according to claim 7 wherein at least about ½ gram of ox bile is used per gram of insoluble cellulose in the first stage.

9. The method according to claim 7 wherein methyl cellulose is mixed together in the dry state with the insoluble cellulose and bile salt, wherein at least about ½ gram of ox bile per gram of insoluble cellulose is used, and wherein the weight of insoluble cellulose is about four times the weight of methyl cellulose.

10. A method for producing a dietary supplement tablet which comprises bile salts permanently bound to an insoluble cellulose matrix, the method comprising the steps of:

(a) in a first stage, forming an activated composition of bile salts and insoluble cellulose by (i) mixing together 165 mgs of desiccated ox bile extract comprising bile salts, 70 mgs of methyl cellulose, and 265 mgs of insoluble cellulose in the dry state;

(ii) forming a suspension of the mixed desiccated ox bile/insoluble cellulose/methyl cellulose in distilled water and adjusting the suspension to a pH of from about 2 to about 4;

(iii) blending the materials in the suspension;

(iv) drying the suspension, while stirring, to provide a partially dry, activated bile salt/insoluble cellulose/methyl cellulose composition having a moisture content of from about 1% by weight to about 3% by weight based on the total dry weight of the composition; and (v) granulating the partially dry, activated composition to provide an activated bile salt/insoluble cellulose/methyl cellulose composition; and (b) in a second stage, mixing the partially dry, activated, granulated bile salt/insoluble cellulose/methyl cellulose composition with 50 mgs of oat fiber, 10 mgs of methyl cellulose, 50 mgs of beet fiber, 50 mgs of apple pectin, and 70 mgs of microcrystalline cellulose to provide a composition comprising bile salts permanently affixed to the insoluble cellulose matrix.

11. The method according to claim 10 wherein the aqueous suspension is dried at a temperature of about 45° C. for about 12 hours.

12. The method according to claim 10 wherein the aqueous suspension is dried at a temperature of about 170° C. for about 1 hour.

13. A method for sequestering fats released from food in a human gastrointestinal tract and promoting the removal of the fats from the body, the method comprising:

(a) introducing a composition comprising insoluble cellulose particles and bile salts into a human gastrointestinal tract, wherein the cellulose particles are of a sufficiently large size so that they will not pass through the intestinal mucosa, and wherein at least a portion of the bile salts are permanently bound to the cellulose particles, the composition formed by a process comprising the steps of:

(i) forming an activated complex of bile salt and insoluble cellulose by mixing together desiccated ox bile comprising bile salts and insoluble cellulose in the dry state to form a bile salt/insoluble cellulose mixture;

(ii) blending the bile salt/insoluble cellulose mixture into distilled water adjusted to a pH of from about 2 to about 4 to form a bile salt/insoluble cellulose suspension;

(iii) drying the bile salt/insoluble cellulose suspension, while stirring, to provide a partially dry, activated bile salt/insoluble cellulose composition having a moisture content not less than 1% by weight of composition;

(iv) granulating the partially dry, activated composition to provide an activated bile salt/insoluble cellulose composition; and (v) mixing the partially dry, activated, granulated composition with microcrystalline cellulose to provide a composition comprising bile salts permanently affixed to the insoluble cellulose particles;

(b) wherein fats released from food in the gastrointestinal tract become attached to the insoluble cellulose/bile salt composition; and (c) wherein the fat-laden insoluble cellulose/bile salt composition passes through the gastrointestinal tract and out of the body with body excreta.

14. The method according to claim 13 wherein the bile salt/insoluble cellulose suspension is stirred at a temperature of about 45° C. for about 12 hours.

15. The method according to claim 13 wherein the partially dry, activated bile salt/insoluble cellulose composition has a moisture content of from about 1% by weight to about 3% by weight compared to the total dry weight of the composition.

16. The method according to claim 13 wherein methyl cellulose is mixed together in the dry state with the insoluble cellulose and desiccated ox bile.

17. The method according to claim 13 wherein at least about ½ gram of ox bile is used per gram of insoluble cellulose to form the activated complex of ox bile and insoluble cellulose.

18. The method according to claim 13 wherein methyl cellulose is mixed together in the dry state with the insoluble cellulose and ox bile, wherein at least about ½ gram of ox bile per gram of insoluble cellulose is used, and wherein the weight of insoluble cellulose is about 4 times the weight of methyl cellulose.

19. A dietary supplement composition comprising bile salts permanently bound to insoluble cellulose, the composition made by a method comprising the steps of:
   (a) in a first stage, forming an activated composition of bile salts and insoluble cellulose by:
      (i) mixing together bile salt and insoluble cellulose in the dry state to form a bile salt/insoluble cellulose mixture;
      (ii) blending the bile salt/insoluble cellulose mixture into distilled water adjusted to a pH of from about 2 to about 4 to form a bile salt/insoluble cellulose suspension; p2 (iii) drying the bile salt/insoluble cellulose suspension to no less than 1% moisture by weight of composition, while stirring, to provide a partially dry, activated bile salt/insoluble cellulose composition; and
      (iv) granulating the partially dry, activated composition to provide an activated bile salt/insoluble cellulose composition; and
   (b) in a second stage, mixing the partially dry, activated, granulated bile salt/insoluble cellulose composition from the first stage with microcrystalline cellulose to provide a composition comprising bile salts permanently affixed to the insoluble cellulose composition.

20. The composition according to claim 19 wherein the bile salt/insoluble cellulose suspension is dried at a temperature of at least 45° C. for from about 1 to about 12 hours.

21. The composition according to claim 19 wherein the bile salt/insoluble cellulose suspension is dried at 45° C. for about 12 hours.

22. The composition according to claim 19 wherein the pH of the bile salt/insoluble cellulose suspension is about 3.

23. The composition according to claim 19 wherein the partially dry, activated bile salt/insoluble cellulose composition has a moisture content of from about 1% by weight to about 3% by weight compared to the total dry weight of the composition.

24. The composition according to claim 19 wherein methyl cellulose is mixed together in the dry state with the insoluble cellulose and desiccated bile.

25. The composition according to claim 19 wherein the bile salt is provided by ox bile.

26. The composition according to claim 25 wherein at least about ½ gram of ox bile is used per gram of insoluble cellulose in the first stage.

27. The composition according to claim 25 wherein methyl cellulose is mixed together in the dry state with the insoluble cellulose and bile salt, wherein at least about ½ gram of ox bile per gram of insoluble cellulose is used, and wherein the weight of insoluble cellulose is about four times the weight of methyl cellulose.

* * * * *